(12) United States Patent
Shi et al.

(10) Patent No.: US 12,071,611 B2
(45) Date of Patent: Aug. 27, 2024

(54) RARE CELL CAPTURE SYSTEM AND APPLICATION THEREOF

(71) Applicants: Chengdu Precisome Biotechnology Co., Ltd., Chengdu (CN); Qiang Xu, Hangzhou (CN)

(72) Inventors: Hubing Shi, Chengdu (CN); Yanchu Li, Chengdu (CN); Qi Xu, Chengdu (CN); Xiangju Kong, Chengdu (CN); Xueyan Wang, Chengdu (CN); Hewen Han, Chengdu (CN)

(73) Assignees: Chengdu Precisome Biotechnology Co., Ltd. (CN); Qiang Xu (CN)

( * ) Notice: Subject to any disclaimer, the term of this patent is extended or adjusted under 35 U.S.C. 154(b) by 847 days.

(21) Appl. No.: 17/255,381

(22) PCT Filed: Jul. 3, 2019

(86) PCT No.: PCT/CN2019/094629
§ 371 (c)(1),
(2) Date: Dec. 22, 2020

(87) PCT Pub. No.: WO2020/001662
PCT Pub. Date: Jan. 2, 2020

(65) Prior Publication Data
US 2021/0269763 A1 Sep. 2, 2021

(30) Foreign Application Priority Data
Jun. 26, 2018 (CN) .......................... 201810666625.X (51) Int. Cl.
*B01L 3/00* (2006.01)
*A61M 1/36* (2006.01)
(Continued)

(52) U.S. Cl.
CPC .......... *C12M 47/04* (2013.01); *A61M 1/3679* (2013.01); *C12N 5/0693* (2013.01); *A61M 2205/0244* (2013.01); *C12N 2509/00* (2013.01)

(58) Field of Classification Search
CPC ................ C12M 47/04; A61M 1/3679; A61M 2205/0244; C12N 5/0693; C12N 2509/00
See application file for complete search history.

(56) References Cited

U.S. PATENT DOCUMENTS

2006/0122552 A1* 6/2006 O'Mahony ........... A61M 1/342
604/6.11
2008/0258657 A1* 10/2008 Ayre ........................ H02P 6/15
318/400.06
(Continued)

FOREIGN PATENT DOCUMENTS

CN 102 258 818 11/2011
CN 102 732 415 10/2012
(Continued)

OTHER PUBLICATIONS https://www.globalspec.com/learnmore/motion_controls/motors/commutators (Year: 2016).*
(Continued)

*Primary Examiner* — Jennifer Wecker
*Assistant Examiner* — Oyeleye Alexander Alabi
(74) *Attorney, Agent, or Firm* — Morrison & Foerster LLP (57) ABSTRACT

Disclosed are a rare cell capture system and an application thereof. The system comprises a fluid tube device, a circulation power apparatus device, a component capture device and an optional anticoagulant release device, the circulation power apparatus device and the component capture device being connected in series to a fluid circulation system via the fluid tube device to form an extracorporeal fluid circulation pathway, the component capture device comprising a micro-
(Continued)

fluidic chip or a chipset. Also disclosed is a method for using the capture system to capture rare cells in blood. The system and the application thereof have the advantages of being large-capacity, in-line and low-hemolysis.

20 Claims, 4 Drawing Sheets

(51) Int. Cl.

| | | |
|---|---|---|
| *B01F 23/00* | (2022.01) | |
| *B01F 23/41* | (2022.01) | |
| *B01F 101/23* | (2022.01) | |
| *B23Q 17/24* | (2006.01) | |
| *C12M 1/00* | (2006.01) | |
| *C12M 1/34* | (2006.01) | |
| *C12N 5/09* | (2010.01) | |
| *C12Q 1/18* | (2006.01) | |
| *G01N 21/3577* | (2014.01) | |
| *G01N 21/359* | (2014.01) | |
| *G01N 21/39* | (2006.01) | |
| *G01N 21/45* | (2006.01) | |
| *G01N 21/64* | (2006.01) | |
| *G01N 33/50* | (2006.01) | |
| *G01N 33/68* | (2006.01) | |

(56) References Cited

U.S. PATENT DOCUMENTS

| | | | | |
|---|---|---|---|---|
| 2011/0155667 A1* | 6/2011 | Charest | ................. | B01D 69/02 |
| | | | | 210/651 |
| 2015/0118728 A1* | 4/2015 | Rahman | ............ | B01L 3/502753 |
| | | | | 422/534 |
| 2015/0285809 A1* | 10/2015 | Barber | ............ | G01N 33/54306 |
| | | | | 506/26 |
| 2017/0225166 A1* | 8/2017 | Toner | ................ | G01N 33/57488 |
| 2018/0100850 A1* | 4/2018 | Takagi | ................. | G01N 33/574 |
| 2019/0016022 A1* | 1/2019 | Liao | ........................ | B29C 33/58 |

FOREIGN PATENT DOCUMENTS

| | | | |
|---|---|---|---|
| CN | 103 382 434 | | 11/2013 |
| CN | 103 732 271 | | 4/2014 |
| CN | 102732415 B | * | 9/2014 |
| CN | 104 745 452 | | 7/2015 |
| CN | 104 815 360 | | 8/2015 |
| CN | 104 906 643 | | 9/2015 |
| CN | 105 311 692 | | 2/2016 |
| CN | 106 955 384 | | 7/2017 |
| CN | 107 148 468 | | 9/2017 |
| CN | 108 795 692 | | 11/2018 |
| WO | WO 2013/003624 | | 1/2013 |
| WO | WO 2014/065861 | | 5/2014 |

OTHER PUBLICATIONS

International Preliminary Report on Patentability of PCT/CN2019/094629, dated Dec. 29, 2020, 6 pages.
Notification to Grant Patent Right for Invention for CN 201810666625.X, dated Nov. 5, 2020, 5 pages.
First Office Action for CN 201810666625.X, dated Jan. 16, 2020, 18 pages.
European Search Report for EP 19826242.0, dated Oct. 12, 2021, 12 pages.
Nagrath et al., "Isolation of rare circulating tumour cells in cancer patients by microchip technology," Nature (2007) 450(7173):1235-1239.
Zhang et al., "Microfluidic-based Tapping and Displacement of Micro Particles," Journal of Mechanical Engineering (2015) 51(14):199-205 (English abstract only).

* cited by examiner

RARE CELL CAPTURE SYSTEM AND APPLICATION THEREOF

CROSS REFERENCE TO RELATED APPLICATIONS

This application is a national stage application under 35 U.S.C. § 371 of International Application No. PCT/CN2019/094629, filed internationally on Jul. 3, 2019, which claims priority to Chinese patent application No. 201810666625.X filed Jun. 26, 2018. The contents of the above patent applications are incorporated by reference herein in their entireties for all purposes.

TECHNICAL FIELD

The present invention relates to biological and pathological body fluid detection, in particular to a system for isolating rare components from a biological body fluid sample and its use thereof, further relates to a system for isolating rare cells from a whole blood cell population and its use thereof, and particularly relates to an on-line system for collecting circulating tumor cells from blood with large-volume and low hemolysis, and its use thereof.

BACKGROUND ART

Rare cells refer to some atypical cells in a biological fluid sample (including blood, pleural fluid, ascites fluid, urine, cerebrospinal fluid, etc.). Studies have shown that the collection of rare cells and using them to complete NGS analysis have important guiding significance for finding potential treatment mechanisms, pathological mechanisms and targeted drug development. The current research methods for detecting rare cells in blood mainly include flow sorting technology, morphological isolation method, density gradient centrifugation, membrane filtration and immunomagnetic isolation technology. For example, BD FACSAris can achieve high-speed cell sorting, but the sorted cells will be damaged by the transient laser in flow sorting, and the cell activity will be damaged after sorting activity. Circulating tumor cells (CTCs) refer to tumor cells that enter the human peripheral blood. Generally, there is few of CTCs in the peripheral blood of cancer patients, only several CTCs (2-10/ml) in blood cells on the order of $10^7$, but CTCs are very important tools for liquid biopsy, prognostic judgment and treatment interval follow-up. As the CTCs are extremely rare, there are quite high requirements on accuracy and specificity of the detection, so that it is even more difficult for further analysis. Therefore, there is an urgent need to develop efficient, high-throughput, and rapid portable methods and tools for isolating CTCs from blood samples.

CTCs in human peripheral blood are circulating tumor cells (CTCs) or cell mass (CTM) disseminated into peripheral blood from tumor foci; the surviving CTCs or CTMs leave the blood circulation and enter the local microenvironment of secondary organs, proliferate and grow and eventually form the metastases under the action of various growth factors. CTCs are an important source of tumor metastasis via blood, while distant metastasis is one of the direct causes of tumor treatment failure, recurrence and death. If the CTCs were detected and intervened at an early stage, the rate of recurrence and metastasis would be significantly reduced. Therefore, the detection of CTCs from the blood has attracted more and more attention. The capture and analysis of CTCs can assist clinicians in predicting and early warning tumor metastasis and recurrence, evaluation of patient overall survival (OS) and progression-free survival (PFS), and monitoring of clinical radiotherapy and chemotherapy efficacy, therefore it has important clinical significance in guiding individualized medical treatment and improving the survival status of tumor patients.

How to more efficiently and accurately use the load of CTCs as a potential predictor to guide the disease course staging and recurrence monitoring of solid tumor patients, and even to obtain the sensitivity information to chemotherapeutic drugs through the culture of CTCs, has become a popular and important topic in cancer research.

However, a prerequisite for clinical diagnosis or laboratory analysis of CTC is the availability of adequate CTCs. Because there is only one CTC per $10^6$ to $10^7$ monocytes in peripheral blood, extremely high requirements are placed on the sensitivity and specificity of CTCs detection technology. At present, various detection schemes of CTCs mainly include a CTCs isolation and enrichment system and a CTCs detection and identification system.

Wherein, Clear-cut system, which is the most representative CTCs isolation and collection system, has been approved by the U.S. FDA for the detection of metastatic breast cancer CTCs. The CellSearch™ system uses magnetic particles labeled with an anti-EpCAM antibody for the capture of CTCs in blood and detects only 10 ml of sampled blood, so that more potential CTCs are not detected with respect to the systemic circulating blood, and there is a selective deviation of the sample. In addition, the samples tested by this method had been left in vitro for several hours, and the cells were in a low oxygen or even hypoxic state. At this time, the captured CTCs had lost their activity, and it was difficult to analyze signal pathways and functionality, and it was impossible to conduct in vitro cell culture and single-cell sequencing.

In recent years, a series of CTCs chip capture technologies have been developed by combining microfluidic chip technology with antibody capture. A microfluidic cell immunochips method, which has the characteristics of high specificity, sensitivity, and repeatability, is a brand-new and efficient method for researching the clinical use value of CTCs, where CTCs are detected by a micro-fluid device, and the captured CTCs with cell activity can be isolated and used for cell culture and other various downstream technical researches. However, there are still defects such as selective deviation of samples due to small volume of blood samples tested by ordinary microfluidic cell immunochips each time.

The identification and characterization of CTC may provide opportunities for studying, monitoring, and ultimately altering the metastasis process. However, it is difficult to isolate CTC from blood without causing rupture or other damage. A major limitation of most existing microfluidic systems is that device efficiency is limited by the shear stress exerted by the device on the blood cells and CTC. Too much shear stress will destroy blood cells and CTC. When the CTC ruptures, the target isolate (the CTC itself) is lost and the inner components of the CTC are scattered into the fluid. The non-specific interactions between species within the blood are further complicated by intracellular material released when the blood cells (primarily leukocytes) rupture, making extraction of high purity CTC more difficult. Some prior devices have attempted to avoid damage to cells, including blood cells and CTCs, by using low-channel microfluidic devices to reduce shear stress. However, a low channel results in a reduced volume of fluid flowing through the channel, which in turn results in a very low flow rate. Such devices are not enough to rapidly process large volumes of blood to make them practical and useful. In view of the extremely low abundance of undamaged CTC in blood, rapid processing of large volume (7 mL to 30 mL) of blood is a prerequisite for the isolation of intact CTC with high yield. At present, none of in-vitro CTCs collection and isolation devices can perform full screening and analysis of whole body blood, and there are problems such as small blood collection samples, insufficient CTCs collection, and selective deviation of samples. The on-line connection of the existing external CTCs collection and isolation device to the in-vivo blood circulation may cause damage to cells in the blood, resulting in a risk of hemolysis; meanwhile, the hemolyzed blood produced by the device will produce cell debris to promote coagulation and reduce blood quality, thereby causing a potential clinical risk. Therefore, there is a need for a portable and on-line CTCs collection system with large-volume and low-hemolysis, which can be connected to the blood circulation in the body to collect CTCs on-line and reduce the risk of hemolysis, so that the processed blood meets the blood reinfusion standards (1. no severe hemolysis; 2. less than 6 h in vitro; 3. unavailable use of liquid that can hemolyze erythrocyte to wash or process blood).

The inventors of the present invention have conducted creative work to provide a tumor cell collection system satisfying the above criteria. The above system has the following advantages: 1. the capture efficiency of CTC is guaranteed, and simultaneously, the hemodynamics and the cell state in blood are guaranteed, so that the blood reinfusion standard is met; 2. the small-range administration of the anticoagulant on the microfluidic chip is adopted, so that the total dosage of the anticoagulant is reduced compared with the whole-body anticoagulant, and the risk of the whole-body anticoagulant is reduced; 3. the blood circulation system can be connected on-line, the analysis amount of a blood sample is enlarged, even CTCs scanning can be performed on whole blood, and the system error caused by selective deviation of the sample is greatly reduced; 4. the improved microfluidic chip technology is adopted, so that damage to blood cells is reduced, and the risk of hemolysis is reduced; 5. the bionic pump simulating cardiac contraction provides circulating power for the system, so that the compress and shearing of blood cells are reduced; 6. the CTCs captured by the microfluidic chip technology can be taken out without damage for analysis or in vitro culture, so that the effects of the CTCs on the aspects of tumor recurrence and drug resistance prediction can be reflected; 7. the system of the present invention not only can capture rare cells by on-line extracorporeal circulation, but also can realize the extracorporeal circulation of fluid off-line, thereby improving the capture efficiency. 8. The system of the present invention can be used to capture not only rare cells in blood, but also various cells, or cellular components, in other biological fluids.

SUMMARY OF THE INVENTION

The present invention aims to provide an on-line large volume circulating rare cell capture system and its use thereof.

In one aspect, the present invention provides a fluid component capture system including a fluid tube device, a circulating power apparatus device, a component capture device and an optionally anticoagulant release device; wherein the circulating power apparatus device and the component capture device are connected in series to a fluid circulating system via the fluid tube device to form an extracorporeal fluid circulating pathway; the component capture device includes a microfluidic chip or a chipset, and an internal corner of the microfluidic chip includes a pin-fin row array.

In one aspect, the present invention provides a fluid component capture system including a fluid tube device, a circulating power apparatus device, a component capture device, and an optionally anticoagulant release device; wherein the circulating power apparatus device and the component capture device are connected in series to a fluid circulating system via the fluid tube device to form an extracorporeal fluid circulating pathway; the component capture device includes a microfluidic chip or a chipset, and all of internal corners of the microfluidic chip are smoothly transitioned curved surfaces.

In one aspect, the present invention provides a fluid component capture system including a fluid tube device, a circulating power apparatus device, a component capture device, and an optionally anticoagulant release device; wherein the circulating power apparatus device and the component capture device are connected in series to a fluid circulating system via the fluid tube device to form an extracorporeal fluid circulating pathway; the component capture device includes a microfluidic chip or a chipset; and the circulating power apparatus device includes a bionic pump simulating cardiac compression.

In one aspect, the present disclosure provides a microfluidic chip.

In one aspect, the present invention provides a circulating power apparatus including a bionic pump simulating cardiac compression to provide power for extracorporeal fluid circulation. According to the preceding aspects, the component is circulating rare cells, preferably CTCs. According to any one of the preceding aspects, wherein the fluid tube device further includes a bypass tube connected in parallel with the component capture device, optionally the bypass tube is provided with a flow-limiting valve or a governor valve which can adjust the flow rate, preferably the flow-limiting valve is a three-way valve.

According to any one of the preceding aspects, wherein an anticoagulant release device is provided between the circulating power apparatus device and the component capture device, the anticoagulant release device includes an anticoagulant sustained releaser, optionally the anticoagulant sustained releaser is connected to the fluid tube via the three-way valve.

According to any one of the preceding aspects, wherein the microfluidic chip body includes a substrate layer and a cover sheet layer which are sequentially arranged from bottom to top, a component capture chamber is arranged between the substrate layer and the cover sheet layer, a fluid inlet and a fluid outlet communicating with the component capture chamber are arranged on the cover sheet layer, the component capture chamber is divided into a buffer zone and a lane portion, and a pin-fin row array is arranged in the lane in a flow direction, wherein the corner surfaces in the component capture chamber are smoothly transitioned curved surfaces, and a person skilled in the art would understand that the corner includes both a concave corner, such as a junction between the upper and the lower wall of the component capture chamber and a side wall, a junction between a bypass flow block or a pin-fin row and the upper and lower wall; and a convex corner, such as a convex angle of the bypass flow block or the pin-fin row in a fluid flow direction. According to any one of the preceding aspects, wherein the buffer zone has a reduced flow rate and a buffering effect as a junction of lanes near the inlet and outlet.

According to any one of the preceding aspects, wherein the lane is divided into two or more lanes arranged in parallel by a bypass flow block, preferably each lane includes 5-500 pin-fin rows, preferably 10-200, further preferably 15-100, such as 15, 16, 17, 18, 19, 20, 21, 22, 23, 24, 25, most preferably 17; optionally, the pin-fin rows are arranged in parallel in the lane at specific intervals of 0.1 to 5, preferably 0.5 to 1 diameter of pin-fin row (long or short diameter).

According to any one of the preceding aspects, wherein the two ends of the bypass flow block respectively form part of the inlet and outlet of the lane, the surface corners of the inlet and outlet are subjected to anti-hemolysis treatment into smoothly transitioned curved surfaces, optionally, the cross section of the inlet and outlet may be circular arc-shaped, rounded, rounded rectangular, rounded trapezoid, etc.

According to any of the preceding aspects, the corner surface of the pin-fin row in a flow direction is a smoothly transitioned curved surface.

According to any one of the preceding aspects, wherein the inner surface of the component capture chamber and the surface of the pin-fin row are loaded with capture ligands that bind to target components in the fluid, preferably the capture ligands are streptavidin-biotin-EPCAM complexes.

According to any of the preceding aspects, the substrate or cover sheet material is selected from silicon, glass, siliconized glass, PDMS, or a high molecular polymer material selected from one or more of polypropylene, a cyclic olefin copolymer, a cyclic olefin polymer, polymethylmethacrylate, and polycarbonate.

According to any one of the preceding aspects, wherein the circulating power apparatus device includes a bionic pump simulating cardiac compression to provide power for extracorporeal fluid circulation, the bionic pump includes: an elastic liner which is provided with an inlet and an outlet at both ends thereof; a torsion member being sleeved on a periphery of the elastic liner; a driving assembly including a power output member which is fixedly connected to the torsion member so as to drive the torsion member to twist when the power output member rotates, to compress or release the elastic liner in a radial direction of the elastic liner, preferably, one-way valves are connected to the inlet and the outlet of the elastic liner to simulate the function of a heart valve and realize the one-way flow of blood.

According to any one of the preceding aspects, wherein the torsion member includes a spirally wound torsion member body, a first end of the torsion member body is fixedly arranged, and a second end of the torsion member body is fixedly connected to the power output member; or the torsion member includes a torsion member body, the torsion member body includes a plurality of member bars which are enclosed in parallel to form a columnar structure, a first end of the torsion member body is fixedly arranged, and a second end of the torsion member body is fixedly connected to the power output member.

According to any one of the preceding aspects, wherein the torsion member further includes a first protective layer covering an inner circumference of the torsion member body; and/or the torsion member further includes a second protective layer covering a periphery of the torsion member body.

According to any one of the preceding aspects, wherein the power output member in the circulating power apparatus device includes a motor, a speed controller and a reversing mechanism, preferably the speed controller is a fully automatic forward and reverse DC motor speed controller, preferably the reversing mechanism is a bevel gear set.

According to any one of the preceding aspects, wherein a forward and reverse interval time and a speed of the motor are controlled through a full-automatic forward and reverse DC motor speed controller, the setting parameters and include: an interval time of forward and reverse rotation of the motor is 0.5 second to 1 second, and a motor speed is 30 revolutions per minute to 60 revolutions per minute.

In one aspect, the present invention relates to a power apparatus for a blood cell collection system, wherein the power apparatus includes:
an elastic liner which is provided with an inlet and an outlet at both ends thereof;
a torsion member being sleeved on a periphery of the elastic liner;
a driving assembly including a power output member which is fixedly connected to the torsion member so as to drive the torsion member to twist when the power output member rotates, to compress or release the elastic liner.

According to any one of the preceding aspects, the torsion member includes a spirally wound torsion member body, a first end of the torsion member body is fixedly arranged, and a second end of the torsion member body is fixedly connected to the power output member; or
the torsion member includes a torsion member body, wherein the torsion member body includes a plurality of bars which are enclosed in parallel to form a columnar structure, a first end of the torsion member body is fixedly arranged, and a second end of the torsion member body is fixedly connected to the power output member.

According to any one of the preceding aspects, wherein the torsion member further includes a first protective layer covering an inner circumference of the torsion member body; and/or the torsion member further includes a second protective layer covering a periphery of the torsion member body.

According to any one of the preceding aspects, wherein the power output member includes an end face perpendicular to a power output axis, and the second end of the torsion member body is fixedly connected to the end face.

According to any one of the preceding aspects, wherein the power output member includes a motor and a reversing mechanism connected to the motor for changing a power output direction of the motor.

According to any one of the preceding aspects, wherein the reversing mechanism is a bevel gear set, the motor is connected to a drive wheel of the bevel gear set, and the end face is located on a driven wheel of the bevel gear set.

According to any one of the preceding aspects, wherein the power output member includes a motor and a flange connected to an output shaft of the motor, and the end face is located on the flange.

According to any one of the preceding aspects, wherein the drive assembly further includes a controller electrically connected to the motor for controlling the motor to perform a forward and reverse rotation operation at set parameters.

A method of capturing rare cells in blood including capturing rare cells in blood by using a fluid component capture system of any of the preceding aspects.

A process according to the preceding aspect including the steps of:
(1) connecting one end of the fluid tube of the fluid component capture system of any one of the preceding claims to a blood sampling device;

(2) connecting the fluid flowing out of the microfluidic chip to a blood transfusion device through a fluid tube;

(3) regulating the flow speed via a flow-limiting valve which is arranged in series or in parallel with the microfluidic chip; and (4) enabling the blood flowing out of the blood sampling device to pass through the circulating power device in the fluid tube and then enter the microfluidic chip for cell capture.

According to the method of the preceding aspect, the blood sampling device may be a blood collection needle or a blood container, and the blood transfusion device may be a blood transfusion needle or a blood container the same as or different from the blood sampling device.

BRIEF DESCRIPTION OF THE DRAWINGS

FIG. 2 is a schematic diagram of circulating power apparatus device.

FIG. 3 is a schematic diagram of a microfluidic chip and its connections.

DETAILED DESCRIPTION OF THE INVENTION

As used herein, the term "rare cells" refer to some atypical cells in a biological fluid sample (including blood, pleural fluid, ascites fluid, urine, cerebrospinal fluid, etc.). Examples of rare cells include, but are not limited to, circulating tumor cells (CTC), circulating endothelial cells (CEC), circulating multiple myeloma cells (CMMC), and circulating melanoma cells (CMC). Preferred rare cells are CTC and CEC, particularly preferred rare cells are CTC. "Circulating tumor cells" (CTC) refer to cancer cells detected in the circulating blood of a subject.

The term "analyte" refers to a molecule or component in a fluid as the target of a method of detection, isolation, concentration, or extraction. Exemplary analytes include cells, viruses, nucleic acids, proteins, carbohydrates, and small organic molecules.

The term "blood component" refers to any component of whole blood, including host erythrocyte, leukocyte, and platelets. Blood components also include plasma components such as proteins, lipids, nucleic acids, and carbohydrates; and for example, any other cells (including rare cells) that may be present in the blood due to current or past pregnancy, organ transplantation, or infection.

The term "fluid" or "biological fluid" is intended to include natural fluids (e.g., blood, lymph, cerebrospinal fluid, urine, cervical lavage fluid, saliva, and water samples), portions of these fluids, and fluids that have been introduced into cells (e.g., culture media and liquid tissue samples). The term also includes lysates.

The term "capture units" or "capture ligands" may refer to the chemical sample used to bind the analyte or the component binding substance on the surface of the whole cell depending on the situation. The capture unit may be a compound coupled to the surface or a material constituting the surface. Typical capture units include antibodies, oligonucleotides or polypeptides, nucleic acids, other proteins, synthetic polymers, and carbohydrates.

The term "channel" or "lane" refers to a gap through which fluid can flow. The channel may be a capillary on a hydrophobic surface, a pipe, or a hydrophilic texture to which an aqueous liquid may be confined.

The term "component" of a cell refers to any component that can be isolated in a cell lysate. The cellular component can be an organelle (e.g., nucleus, paranuclear compartment, nuclear membrane, mitochondria, chloroplast, or cell membrane), a polymer or molecular complex (e.g., lipids, polysaccharides, (membrane, transmembrane or cytoplasmic) proteins, (natural, therapeutic, or pathogenic) nucleic acids, viral particles, or ribosome), or other molecules (e.g., hormones, ions, cofactors, or drugs). "Component" of a cellular sample refers to a subset of cellular components contained in the sample.

The term "enriched samples" refer to samples containing analytes, which have been processed to increase the relative content of the analytes compared to samples normally present. For example, the samples can be enriched by increasing the amount of target analyte by a factor of at least 10%, 25%, 50%, 75%, 100%, or at least 10, 100, 1000, 10,000, 100,000, or 1,000,000 times. The term "section" refers to a profile side view image.

The term "rare amount" of cells refers to less than 100 cells/ml of fluid, less than 10 cells/ml of fluid, or even less than 1 cell/ml of fluid.

Still other features and advantages will be apparent from the following description and claims.

In order to achieve the purpose of the present invention, the inventors have conducted creative work to provide a technical scheme of a fluid cell capture system, wherein the system includes a fluid tube device, a cell capture device and a circulating power apparatus device; the fluid tube device can be connected into a fluid circulating system to form an extracorporeal fluid circulating pathway, and the cell capture device is connected to the fluid tube in series or in parallel, so that the fluid can pass through the cell capture device to capture cells contained in the fluid; and the circulating power apparatus device provides power for extracorporeal fluid circulation. Optionally, the fluid cell capture system further includes an anticoagulant release device which is an anticoagulant sustained releaser having a flow control infusion pump, and the anticoagulants include but not limited to common anticoagulants such as EDTA, citric acid or heparin. Preferably, the fluid is blood. Preferably, the cells are circulating rare cells, and further preferably, the cells are CTCs. The cell capture device includes a microfluidic chip or chipset.

In one embodiment, the chip body includes a substrate layer and a cover sheet layer sequentially arranged from bottom to top, a component capture chamber is arranged between the substrate layer and the cover sheet layer, a fluid inlet and a fluid outlet communicating with the component capture chamber are arranged on the cover sheet layer, the component capture chamber is divided into a buffer zone and a lane portion, the buffer zone has a reduced flow rate and a buffering effect as a junction of lanes near the inlet and outlet; the lane portion includes one or more lanes, preferably is divided into at least two lanes by a bypass flow block, in which a pin-fin row array is arranged in a flow direction.

In one embodiment, the two ends of the bypass flow block respectively form part of the inlet and outlet of the lane, and the corner surface of the inlet and outlet is subjected to anti-hemolysis treatment into a smoothly transitioned curved surface, for example, the cross section of the inlet and outlet can be arc-shaped, rounded, rounded rectangle, rounded trapezoid, etc.

In one embodiment, the cross section of the pin-fin row is streamlined, spindle-shaped, dumbbell-shaped or similar to the tail-to-tail shape of two water droplets, so that the surface in the flow direction is a smoothly transitioned curved surface, thereby reducing damage to cells in the fluid by mechanical shear forces. A height of the pin-fin row array is equal to the interior height of the chipset component capture chamber.

In one embodiment, the pin-fin rows are disposed at one side of the cover sheet adjacent the substrate.

In one embodiment, the pin-fin row is disposed at one side of the substrate adjacent the cover sheet.

In one embodiment, each lane has a diameter of 3 mm to 5 mm, a height of 50 µm to 100 µm, a pin-fin row spacing of 0.1 to 5 column diameters, preferably 0.5 to 1 column diameter, and a height of column array of 10 µm to 100 µm, with 50 to 500 columns forming a microarray in each lane.

In one embodiment, the lanes are arranged in parallel.

In one embodiment, the substrate has a length of 5 mm to 100 mm, preferably 20 mm to 80 mm, further preferably 30 mm to 60 mm, most preferably 50 mm; has a width of 5 mm to 50 mm, preferably 10 mm to 30 mm, most preferably 20 mm.

In one embodiment, the number of lanes is 1 to 20, preferably 4 to 15, further preferably 6 to 10, most preferably 8.

In one embodiment, the lane has a length of 5 mm to 100 mm, preferably 20 mm to 40 mm, most preferably 30 mm; a width of 0.1 mm to 50 mm, preferably 0.5 mm to 5 mm, further preferably 1 mm to 3 mm, most preferably 1.5 mm; has a height of 0.05 mm to 0.5 mm, preferably 0.05 mm to 0.1 mm.

In one embodiment, the substrate or cover sheet material is selected from silicon, glass, siliconized glass, PDMS, or a high molecular polymer material selected from one or more of polypropylene, a cyclic olefin copolymer, a cyclic olefin polymer, polymethylmethacrylate, and polycarbonate.

In one embodiment, the cell capture device includes a chip combiner that is a medical grade connection pipe and a card slot for receiving a microfluidic chip such that a plurality of chips is connected in parallel or in series to form a chipset.

In one embodiment, the inner surface of the component capture chamber and the surface of the pin-fin row are loaded with streptavidin which is capable of specifically binding to labeled biotin in an epithelial cell adhesion molecule (EPCAM)-biotin complex, the EPCAM-biotin complex is capable of specifically binding to a unique antigen on the surface of CTCs, wherein the link of the streptavidin-biotin complex in the streptavidin-biotin-EPCAM complex has the ability to be eluted competitively by high concentration of biotin. Optionally, other capture ligands, such as antigens, antibodies, Protein A, Protein G, lectins, etc., may also be coated on the inner surface of the component capture chamber and the surface of the pin-fin row.

In one embodiment, the circulating power apparatus device includes an elastic liner which is provided with an inlet and an outlet at both ends thereof; a torsion member being sleeved on a periphery of the elastic liner; a driving assembly including a power output member which is fixedly connected to the torsion member so as to drive the torsion member to twist when the power output member rotates, to compress or release the elastic liner.

In one embodiment, the torsion member includes a spirally wound torsion member body, a first end of the torsion member body is fixedly arranged, and a second end of the torsion member body is fixedly connected to the power output member; or the torsion member includes a torsion member body, the torsion member body includes a plurality of member bars which are enclosed in parallel to form a columnar structure, a first end of the torsion member body is fixedly arranged, and a second end of the torsion member body is fixedly connected to the power output member.

In one embodiment, the torsion member further includes a first protective layer covering an inner circumference of the torsion member body; and/or the torsion member further includes a second protective layer covering a periphery of the torsion member body.

In one embodiment, the power output member includes an end face perpendicular to a power output axis, and the second end of the torsion member body is fixedly connected to the end face.

In one embodiment, the power output member includes a motor and a fully automatic forward and reverse DC motor speed controller and a reversing mechanism, wherein the reversing mechanism is connected to the motor for changing a power output direction of the motor.

In one embodiment, the reversing mechanism is a bevel gear set, the motor is connected to a drive wheel of the bevel gear set, and the end face is located on a driven wheel of the bevel gear set.

In one embodiment, the power output member includes a motor and a flange connected to an output shaft of the motor, and the end face is located on the flange.

In one embodiment, the drive assembly further includes a controller electrically coupled to the motor for controlling the motor to perform a forward and reverse rotation operation at set parameters.

In one embodiment, a forward and reverse interval time and a speed of the motor are controlled through a full-automatic forward and reverse DC motor speed controller, the setting parameters and include: an interval time of forward and reverse rotation of the motor is 0.5 second to 1 second, and a motor speed is 30 revolutions per minute to 60 revolutions per minute.

In one embodiment, a protective layer is arranged on the inner circumference of the torsion member body, which can effectively increase the contact area of the torsion member main body with the elastic liner during the torsion process, thereby making the force received by the elastic liner more uniform and realizing uniform compression or relaxation of the elastic liner.

In one embodiment, the torsion member is fixed to the end face of the flange or bevel gear, and then the motor output shaft is connected to the flange or bevel gear, so that the axis of the power output shaft can be matched with the center line of the torsion member, thereby avoiding the phenomenon of vibration caused by the offset of the connection point of the torsion member and the power output shaft from the axis of the output shaft, and enabling the power device of the system to stably drive.

In one embodiment, a one-way valve is connected to the inlet and the outlet of the elastic liner to simulate the function of a heart valve, so that the one-way flow of blood is realized, thereby avoiding the phenomenon of blood backflow in the circulation process to protect the blood cells in the blood well.

According to the power device of the present invention, the torsion member and the elastic liner are detachably designed, which realizes the modularization and miniaturization of the device; compared with a peristaltic pump, the elastic liner serving as a blood chamber is an enlarged and elastic device in a circulating system, which can effectively reduce the change of hemodynamic shear force in a blood circulating process, thus avoiding the compress of erythrocyte in a flexible pipe by the peristaltic pump, and greatly reducing the risk of hemolysis. Due to the fact that the torsion member is arranged, the elastic inner liner is compressed and released by the deformation of the torsion member, the interval time and the rotating speed of the forward and the reverse rotation of the motor are controlled through the driving of the motor running under set parameters, namely the full-automatic forward and reverse direct current motor speed controller, enabling the elastic inner liner to contract or relax in the same or similar motion pattern and rhythm as the heartbeat. While ensuring the efficiency of CTCs capture, the bionic drive of the power device is realized, so that the power device can simulate the heart pumping mode, avoiding the phenomenon of cell damage caused by excessive squeezing of the soft pipe in the prior art, thereby ensuring the integrity of the cells during the transportation process, reducing the destruction of blood cells by the blood collection system during the blood collection process, and greatly reducing the risk of hemolysis.

In one embodiment, the anticoagulant release device is an anticoagulant sustained releaser, preferably a front-end miniaturized anticoagulant sustained releaser, meaning that the miniaturized anticoagulant sustained releaser is positioned before blood entering the microfluidic chip to ensure an anticoagulant state within the microfluidic chip.

In one embodiment, the sustained releaser may be a conventional medical analgesia pump known in the prior art. The whole device is made of medical grade plastic, which is portable and has the property of releasing heparin sodium at a constant speed to ensure the anticoagulation in the environment of the microfluidic chipset.

Figure 1:
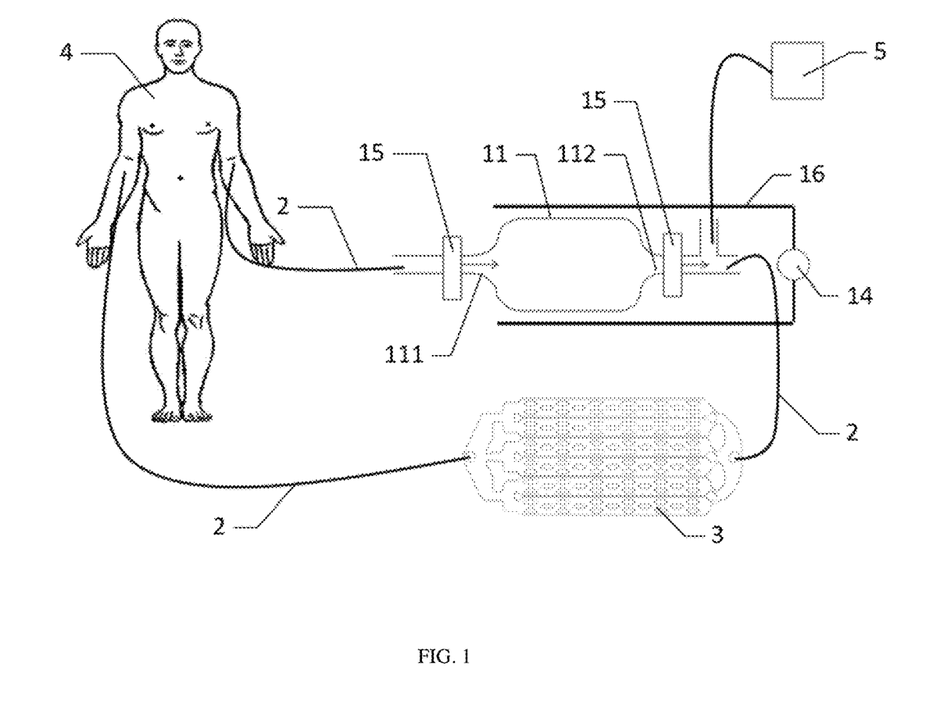
FIG. 1 is a schematic diagram of a fluid component capture system, wherein 11: elastic liner, 111: power apparatus inlet, 112: power apparatus outlet, 2: fluid tube, 3: cell capture device, 4: human body, and 5: anticoagulant release device.
Figure 2A:
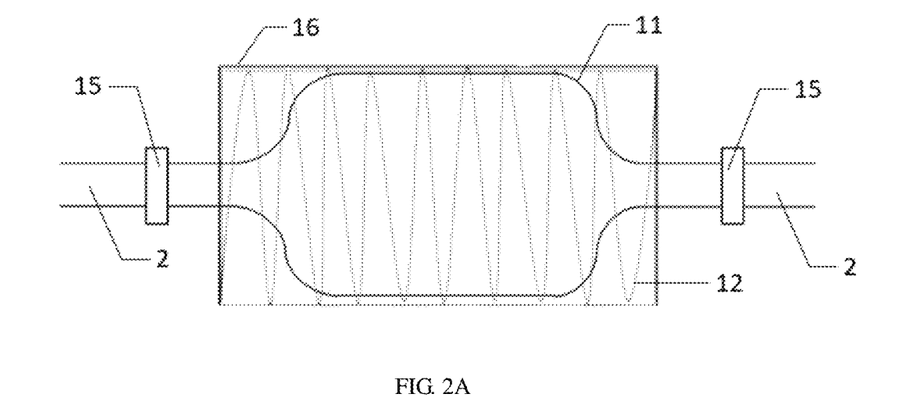
FIG. 2A is an embodiment of a torsion member.
Figure 2B:
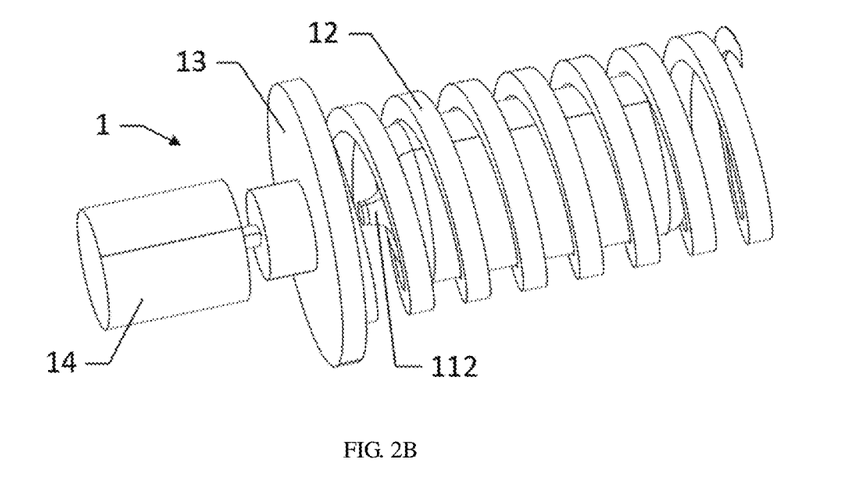
FIG. 2B is a schematic diagram of one embodiment of a circulating power apparatus device, wherein 1: circulating power apparatus device, 2: fluid tube, 11: elastic liner, 12: torsion member body, 13: flange, 14: motor, 15: check valve, 16: second protective layer, and 112: power apparatus outlet.
Figure 2C:
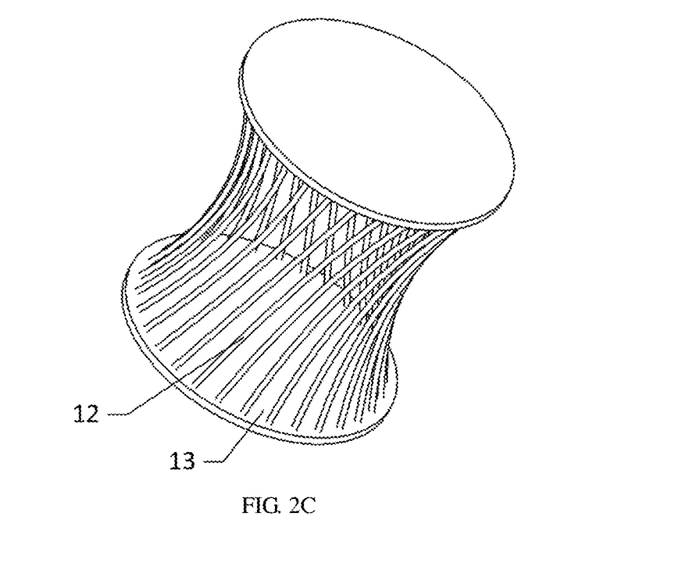
FIG. 2C is a schematic diagram of another embodiment of a circulating power apparatus device, wherein 12: torsion member body and 13: flange.
Figure 3A:
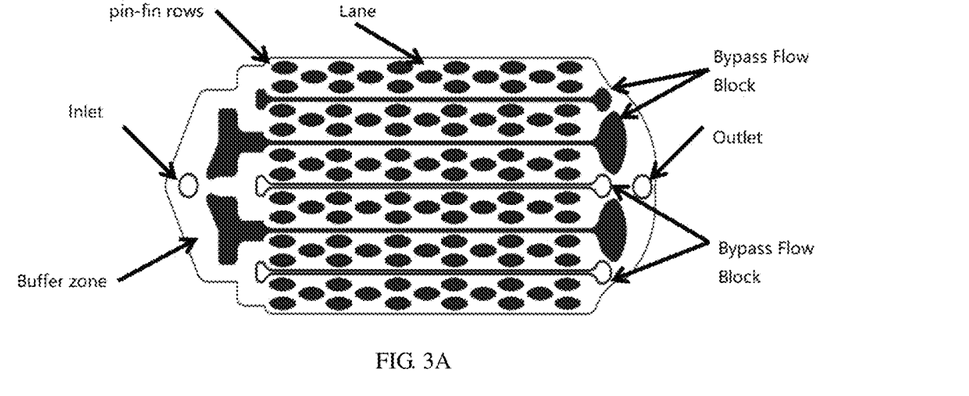
FIG. 3A is a schematic diagram of one embodiment of a microfluidic chip.
Figure 3B:
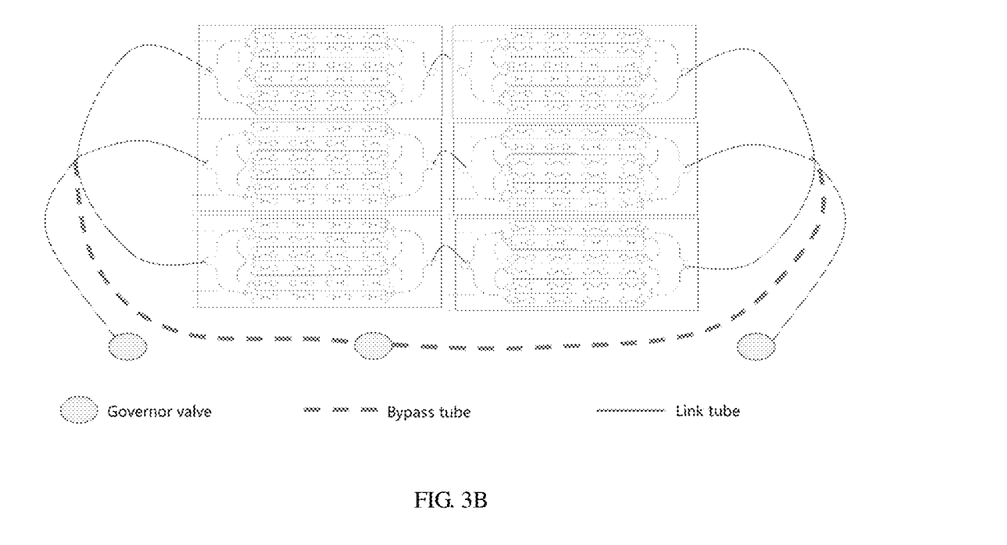
FIG. 3B is a schematic diagram of a microfluidic chipset and bypass channel connections.

According to the microfluidic chipset disclosed by the present invention, the microfluidic chipset is connected into the system in a serial or parallel mode according to the requirement of actual blood sampling quantity. Blood enters the circulating power system to obtain extracorporeal circulation power after being guided out by blood vessels, is bifurcated into one or more parallel pipes at the far end, is respectively connected into the microfluidic chipset and the bypass, and is provided with a flow-limiting valve after entering the microfluidic chipset. The connection is shown in FIG. 3. Preferably, the flow-limiting valve is a three-way flow-limiting valve. Due to the arrangement of the bypass tube, the flow rate and the pressure passing through the component capturing chamber can be conveniently adjusted, high shearing force cannot be easily generated on blood cells, hemolysis is prevented, and pipe blockage cannot be easily caused.

The microfluidic chip or the chipset is connected into the blood circulation system, and the anticoagulant sustained releaser is connected in the form of a three-way pipe. The anticoagulant sustained releaser is internally provided with an elastic automatic contraction pump to contract and compress the anticoagulant at a constant speed, ensuring the anticoagulant is pumped uniformly; a one-way valve is arranged in the anticoagulant device to prevent blood in the microfluidic chip from circulating back into the anticoagulant device; the anticoagulant device contains heparin sodium anticoagulant. An anticoagulant sustained releaser is provided so that a pumping speed of the anticoagulant is a constant value, and an output quantity is adjusted according to a total volume of blood required to be collected; after the infusion pump switch is turned on, the pump body works and pumps out the anticoagulant continuously in a constant amount. The anticoagulant is mixed with circulating blood and then passes through a microfluidic chip micro-channel to be contacted with the antibody loaded on the surface of the micro-channel, the CTCs are captured from the blood sample and fixed on the surface of the micro-channel by utilizing the binding of the antibody loaded on the surface of the micro-channel to the specific antigen on the surface of the CTCs, and the circulating collection is continued for 1 h to 10 h.

In one embodiment, the antibody and the captured CTCs are released from the surface of the microchannel by cleaving the streptavidin-biotin complex, thereby obtaining CTCs of high purity, and cleaning the microfluidic chip with a cell washing solution after the circulating collection is completed, thereby collecting the captured CTCs. The cell cleaning solution is a buffer solution containing high-concentration biotin protein, and a preservative can be added according to preservation requirements. The eluted CTCs may be stained with CD45 and CK8/18 fluorescent antibody, and the cell population of CD 45 (−) and CK8/18(+) is determined as CTCs through fluorescence microscope observation.

Figure 4:
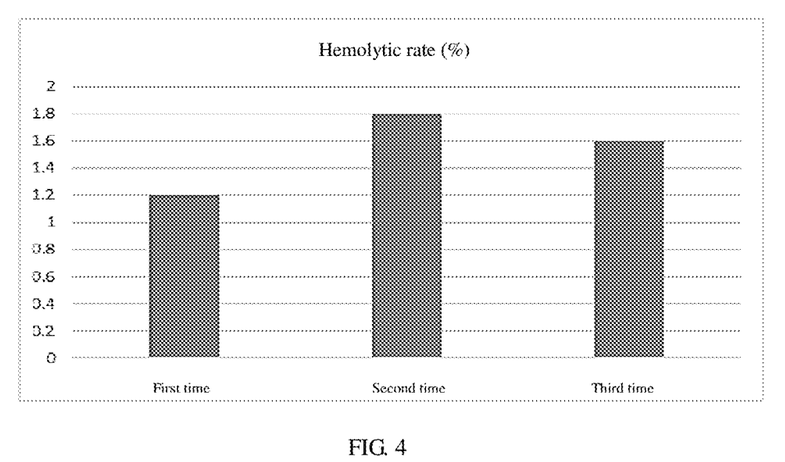
FIG. 4 shows the detection of hemolysis by spectrophotometry.

Low hemolysis described in the present disclosure is verified by the measured erythrocytic hemolysis after the anticoagulated blood tested by the "spectrophotometric method" after passing through the chip of the present disclosure (FIG. 4).

Compared with the prior art, the present invention has the following advantages and characteristics:

1. The existing system only analyzes a small amount of blood samples. With respect to the total blood volume of 4000 ml in the whole body, the sample volume of the existing system is too small, which may cause selective offset errors and false negative rates. The samples of the present invention can cover the whole body blood and solve the problem that the whole body blood cannot be scanned and detected by the current CTCs collection scheme, which greatly reduces the systematic error caused by the selective deviation of the sample. 2. Compared with the method for CTCs capture based on a targeted polypeptide and a microfluidic chip, the present invention does not need to perform erythrocyte lysis before collecting CTCs, but instead protects erythrocyte during the process of collecting CTCs. 3. the streptavidin-biotin complex of the present invention can be broken by the cell cleaning solution, and the CTCs captured by the microfluidic chip technology can be taken out non-destructively for further analysis or in vitro culture, which will be able to better play the role of CTCs. 4. The inlets and outlets of the lanes in microfluidic chipset and connecting pipes are designed as smoothly transitioned curve, which avoids potential damage to blood cells caused by the internal structure of the system. 5. The pin-fin row array increases the surface area in contact with blood and also prevents mechanical damage to blood cells; compared with existing CTCs detection or blood cell removal devices, the pin-fin row chip designed by this invention is more suitable for on-line blood collection systems, performs blood collection in the form of a chipset to ensure efficient CTCs collection, and also reduces the occurrence of blood hemolysis to ensure the quality of blood after circulation. 6. The system of the present invention can not only capture rare cells by on-line extracorporeal circulation, but also can realize off-line extracorporeal circulation of fluid, thereby improving the capture efficiency. 7. The system of the present invention can be used not only to capture rare cells in blood, but also to capture various cells or cell components in other biological fluids.

EXAMPLES

The present invention is further illustrated by the following examples.

Example I: Detection of Capture Ability of CTCs in Breast Cancer

1. Surface coating of streptavidin 1.1 The chip was washed three times with 200 UL sterile PBS to determine that no air bubbles remained in the chip channels.

100 μL of streptavidin protein was injected into the chip by a syringe, and then the chip was placed in a wet box and coated at 37° C. for 2 h.

2. Coating capture antibody 2.1 Human-EpCAM capture antibody (biotin-labeled) was added to 1×PBS sterile solution and mixed well to prepare 5 μg/ml antibody capture working solution.

2.2 100 μL of antibody capture working solution was injected into the chip by a syringe, then the chip was placed in a wet box and incubated at 4° C. overnight, ensuring that all chip flow channels are always covered with the antibody capture working solution during the whole incubation process.

2.3 The capture antibody coated chip was washed three times with 200 μL of 1×PBS sterile solution to remove the capture antibody working solution remained in the chip.

2.4 Chips were blocked with 200 μL of 5% BSA solution at 27° C. for 2 h.

2.5 At this point, the coating of the capture antibody on the chip was completed and ready to use 3. Capture of CTCs 3.1 The power section of the device was connected into a container containing 10 ml of blood from a patient with breast cancer. After blood was exported out through blood vessels, the blood entered a power device system (including a motor and a bionic pump) to obtain extracorporeal circulation power, and then was connected into a blood circulation system consisting of a microfluidic chipset.

3.2 A microfluidic chipset formed in a parallel/series mode was connected through a medical-grade pipe, and then an automatic front-end anticoagulant sustained releaser was turned on.

3.3 A power switch was turned on, and the cell suspension was collected uninterrupted and cyclically for 1 h.

3.4 A power switch of the device was turned off, and the automatic front-end anticoagulant sustained releaser was turned off for finishing collection of CTCs.

3.5 The chip was washed three times with 200 μL of 1×PBS sterile solution.

5. Observation of CTCs and hemolysis

Figure 5A:
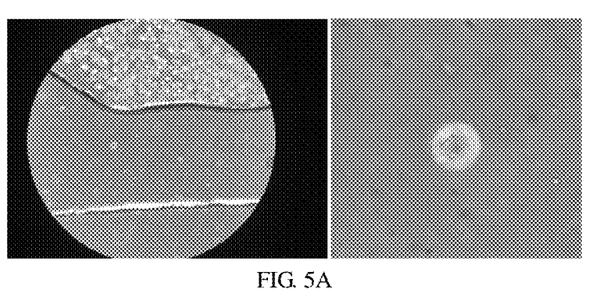
FIG. 5 shows the collection of CTCs.
Figure 5B:
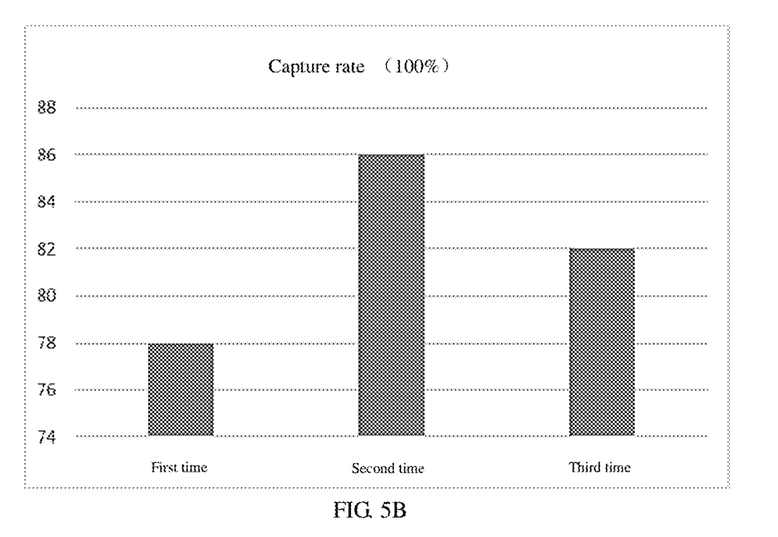

The number of collected CTCs was observed under a microscope; CTCs were judged according to cell morphology size and nucleo-cytoplasmic ratio (FIG. 5).

The hemolysis of erythrocyte in the blood after circulation was detected by "spectrophotometry", and no abnormal increase in hemoglobin value was found (FIG. 4).

Example II: Detection of Capture Efficiency of Breast Cancer Cells

1. Surface coating of streptavidin 1.1 The chip was washed three times with 200 μL sterile PBS to determine that no air bubbles remained in the chip channels.

100 μL of streptavidin protein was injected into the chip by a syringe, and then the chip was placed in a wet box and coated at 37° ° C. for 2 h.

2. Coating capture antibody 2.1 Human-EpCAM capture antibody (biotin-labeled) was added to 1×PBS sterile solution and mixed well to prepare 5 μg/ml antibody capture working solution.

2.2 100 μL of antibody capture working solution was injected into the chip by a syringe, then the chip was placed in a wet box and incubated at 4° C. overnight, ensuring that all chip flow channels are always covered with the antibody capture working solution during the whole incubation process.

2.3 The capture antibody coated chip was washed three times with 200 μL of 1×PBS sterile solution to remove the capture antibody working solution remained in the chip.

2.4 Chips were blocked with 200 μL of 5% BSA solution at 27°C for 2 h.

2.5 At this point, the coating of the capture antibody on the chip was completed and ready to use 3. Capture of CTCs 3.1 The power section of the device was connected into a MCF7 breast cancer cell suspension system (simulated blood system, 100 ml in volume, 100 cells in the system). After blood was exported out through blood vessels, the blood entered a power device system (including a motor and a bionic pump) to obtain extracorporeal circulation power, and then was connected into a blood circulation system consisting of a microfluidic chipset.

3.2 A microfluidic chipset formed in a parallel/series mode was connected through a medical-grade pipe, and then an automatic front-end anticoagulant sustained releaser was turned on.

3.3 A power switch was turned on, and the cell suspension was collected uninterrupted and cyclically for 1 h.

3.4 A power switch of the device was turned off, and the automatic front-end anticoagulant sustained releaser was turned off for finishing collection of CTCs.

4. Elution of CTCs 4.1 The chip was washed three times with 200 μL of 1×PBS sterile solution.

4.2 The number of collected MCF7 cells was observed under a microscope;

4.2 200 μL of cell cleaning solution (containing high-concentration biotin) was injected into the chip by a syringe, standing at room temperature for 30 min, the streptavidin-biotin complex, was isolated to release the biotin-EPCAM complex.

4.3 The chip was washed three times with 200 μL of 1× sterile PBS and the cell cleaning solution was collected.

5 Observation of CTCs 5.1 The collected CTCs were fixed with 200 μL of 95% ethanol by a syringe for 30 minutes.

5.2 The remaining detection antibody mixture was removed by washing 3 times with 200 μL of 1× sterile PBS solution.

5.3 CTCs were stained for CK8 and CD45 fluorescence and observed under a fluorescence microscope. CK8 (+) and CD45 (−) indicated that the cells were tumor cells, demonstrating device capture efficiency.

The present invention can be used for on-line large-volume detection of CTCs in peripheral blood of a patient with breast cancer. By scanning as much blood as possible, the detection sensitivity of CTCs of breast cancer is improved, especially by using a microfluidic chipset, the detection sensitivity of CTCs of breast cancer is significantly improved. Meanwhile, on the basis of scientific research field and clinical test verification, epithelia-derived CTCs in peripheral blood of patients with breast cancer can be effectively detected by using a method of immunologically identifying specific cytokeratin CK, leukocyte common antigen CD 45 and cell nucleus plus cell morphology staining of CTCs.

It is intended that the present invention is not be limited to the particular embodiments shown and described herein, but that various changes and modifications may be made without departing from the spirit and scope of the present invention as defined by the specification.

What is claimed is:

1. A fluid component capture system, comprising a fluid tube device, a circulating power apparatus device, and a component capture device, wherein the circulating power apparatus device and the component capture device are connected in series to a fluid circulating system via the fluid tube device to form an extracorporeal fluid circulating pathway, the fluid tube device further comprises a bypass tube connected in parallel with the component capture device, the bypass tube is provided with a flow-limiting valve configured to adjust the flow rate; the component capture device comprises a microfluidic chip or a chipset, the flow-limiting valve which is arranged in series or in parallel with the microfluidic chip, the microfluidic chip comprises a substrate layer and a cover sheet layer sequentially arranged from bottom to top, a component capture chamber is arranged between the substrate layer and the cover sheet layer, a fluid inlet and a fluid outlet communicating with the component capture chamber are arranged on the cover sheet layer, the component capture chamber is divided into a buffer zone and a lane portion, the lane portion is divided into two or more lanes arranged in parallel by setting a bypass flow block, and a pin-fin array is arranged in the lane in a flow direction, the pin-fin rows are arranged in parallel in the lane at specific intervals of 0.5 to 1 diameter of pin-fin row.

2. The system according to claim 1, wherein all of internal corners of the microfluidic chip are smoothly transitioned curved surfaces.

3. The system according to claim 1, wherein the circulating power apparatus device comprises a bionic pump simulating cardiac compression.

4. The system according to claim 1, wherein an anticoagulant release device is provided between the circulating power apparatus device and the component capture device, the anticoagulant release device comprises an anticoagulant sustained releaser.

5. The system according to claim 1, wherein the inner surface of the component capture chamber and the surface of the pin-fin row are loaded with capture ligands that bind to target components in the fluid.

6. The system according to claim 1, wherein a power output member in the circulating power apparatus device comprises a motor, a speed controller and a reversing mechanism.

7. A method of capturing rare cells in blood, comprising capturing rare cells in blood by using the fluid component capture system according to claim 1.

8. The system according to claim 1, wherein the flow-limiting valve is a three-way valve.

9. The system according to claim 4, wherein the anticoagulant sustained releaser is connected to the fluid tube device via the three-way valve.

10. The system according to claim 5, wherein the capture ligands are streptavidin-biotin-anti-EPCAM antibody complexes.

11. The system according to claim 6, wherein the speed controller is a fully automatic forward and reverse DC motor speed controller.

12. The system according to claim 6, wherein the reversing mechanism is a bevel gear set.

13. The system according to claim 6, wherein the motor is in forward and reverse rotation with an interval time of 0.5 second to 1 second and a motor speed of 30 revolutions per minute to 60 revolutions per minute.

14. The method of claim 7, comprising the steps of:
(1) connecting one end of the fluid tube device of the fluid component capture system of any one of the preceding claims to a blood sampling device;
(2) connecting the fluid flowing out of the microfluidic chip to a blood transfusion device through a fluid tube;
(3) regulating a flow speed via a flow-limiting valve which is arranged in series or in parallel with the microfluidic chip; and
(4) enabling the blood flowing out of the blood sampling device to pass through the circulating power device in the fluid tube and then enter the microfluidic chip for cell capture.

15. The system according to claim 1, wherein each lane includes 5-500 pin-fin rows.

16. The system according to claim 2, wherein each lane includes 15, 16, 17, 18, 19, 20, 21, 22, 23, 24, 25 pin-fin rows.

17. The system according to claim 1, wherein the system further comprises an anticoagulant release device.

18. The system according to claim 17, wherein the fluid tube device further comprises a bypass tube connected in parallel with the component capture device.

19. The system according to claim 15, wherein each lane includes 15-100 pin-fin rows.

20. The system according to claim 16, wherein each lane includes 17 pin-fin rows.

* * * * *